United States Patent [19]

Springer et al.

[11] 4,193,289

[45] Mar. 18, 1980

[54] CERAMIC INSULATOR FOR AN EXHAUST GAS OXYGEN SENSOR

[75] Inventors: Jerry L. Springer; Charles M. Wells, both of Livonia; Wells L. Green, Garden City, all of Mich.

[73] Assignee: Ford Motor Company, Dearborn, Mich.

[21] Appl. No.: 5,421

[22] Filed: Jan. 22, 1979

[51] Int. Cl.$^2$ .............................................. G01N 7/02
[52] U.S. Cl. ................................................... 73/27 R
[58] Field of Search ................................. 73/23, 27 R

[56] References Cited

U.S. PATENT DOCUMENTS

| | | | |
|---|---|---|---|
| 3,886,785 | 6/1975 | Stadler et al. | 73/23 |
| 3,932,246 | 1/1976 | Stadler et al. | 73/27 R X |
| 3,959,765 | 5/1976 | Stewart | 338/34 |
| 4,012,709 | 3/1977 | Logothetis et al. | 73/23 X |
| 4,151,503 | 4/1979 | Cermak et al. | 73/27 R X |
| 4,162,631 | 7/1979 | Logothetis et al. | 73/362 A R |

Primary Examiner—Gerald Goldberg
Assistant Examiner—Joseph W. Roskos
Attorney, Agent, or Firm—Robert W. Brown; Clifford L. Sadler

[57] ABSTRACT

An improved exhaust gas oxygen sensor of the type adapted for installation in an exhaust conduit of an internal combustion engine. The improved sensor is of the type employing a titania oxygen sensing element responsive to the partial pressure of oxygen in the exhaust gas. A ceramic insulator supports the titania oxygen sensing element and is of improved design. Prior designs have contributed to cold-working of the electrode lead wires connected to the titania oxygen sensing element. The improved insulator design has a pedestal located adjacent the passages in the insulator through which the lead wires pass for the purpose of minimizing cold-working of the lead wires. This aids in preventing fracture of the wires during their use in a feedback fuel control system employing the oxygen sensor.

4 Claims, 4 Drawing Figures

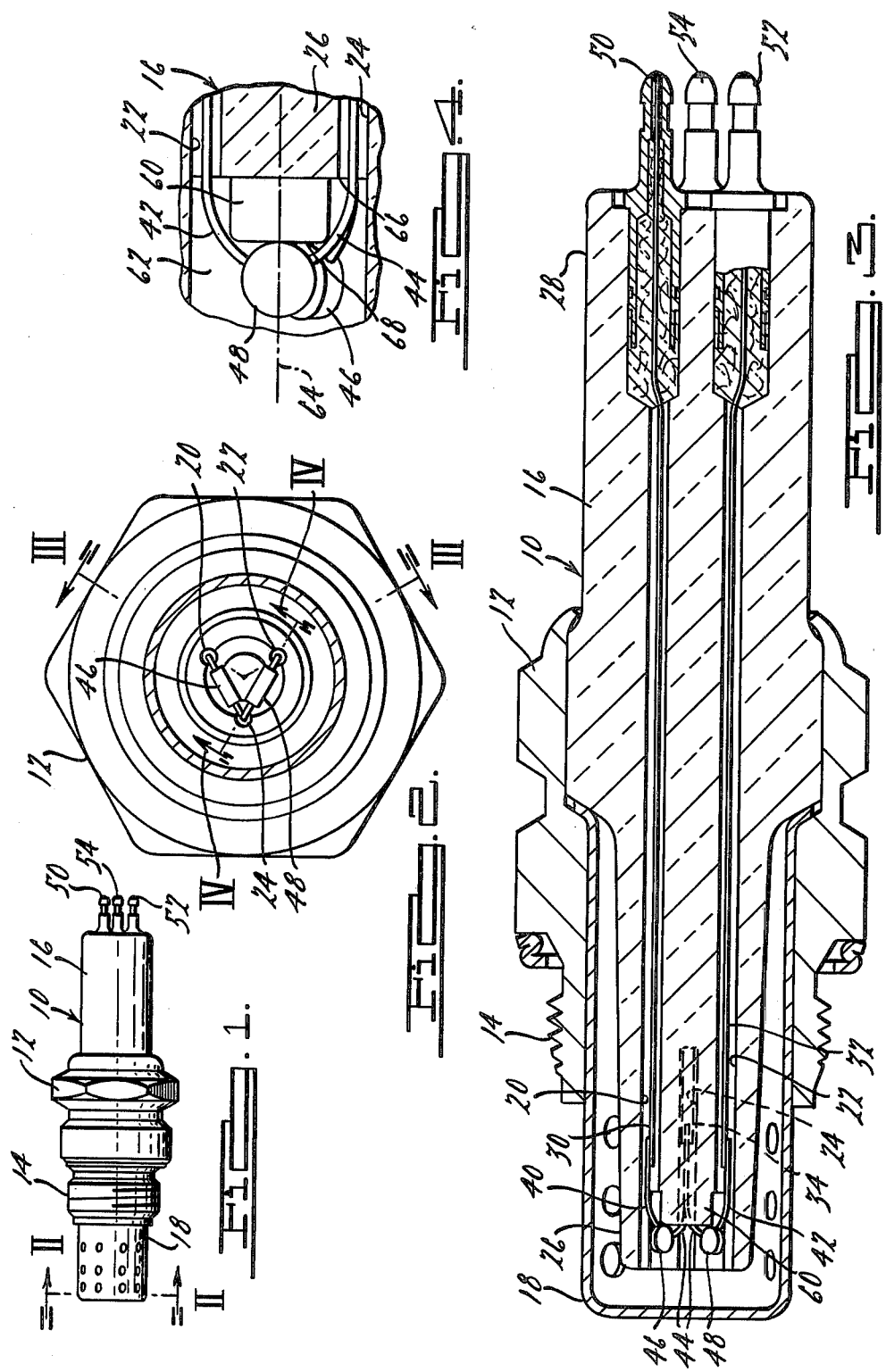

CERAMIC INSULATOR FOR AN EXHAUST GAS OXYGEN SENSOR

BACKGROUND

This invention relates to an improved exhaust gas oxygen sensor of the type adapted for installation in a conduit for conveying exhaust gases from an internal combustion engine. The improved sensor is responsive to the partial pressure of oxygen in the exhaust gases to which the sensor is exposed and has an electrical characteristic which varies, when the sensor is at operating temperatures in the range from 350° C. to about 850° C., with the partial pressure of oxygen in the exhaust gases. The invention particularly relates to an improved ceramic insulator used in an exhaust gas sensor of the type employing a metal oxide ceramic material, such as titania, as the oxygen sensing element having precious-metal electrode lead wires passing through passages formed in the ceramic insulator material.

Exhaust gas sensors of the type to which the present invention relates have been fabricated with a titania oxygen sensing element of disc shape having electrode lead wires embedded therein. The lead wires convey to an electronic control system an electrical signal that results from variations in the electrical resistance of the titania disc. The titania resistance changes are produced by corresponding variations in the composition of the exhaust gases to which the sensor is exposed. The electrical lead wires and the titania oxygen sensing element to which they are connected are supported by a ceramic insulator mounted within a steel body that is attached to an exhaust conduit of the engine. The varying electrical signal generated by the titania oxygen sensing element are transmitted by its precious metal electrode lead wires to other lead wires in the ceramic insulator. These other lead wires are connected to terminal pins located at the end of the ceramic insulator.

It has been found that bending of the precious metal oxygen sensing element electrode lead wires, comprised of platinum as the major constituent, produces cold-working of the lead-wire metal that can cause the effected areas to fail by fracture after use in an exhaust gas environment. Failure of the lead wires of the sensor renders it useless.

SUMMARY OF THE INVENTION

The exhaust gas oxygen sensor of the invention is designed to be used with a ceramic oxygen sensing element having electrode lead wires embedded within it. The oxygen sensing element and its lead wires are supported by a projecting portion of a ceramic insulator mounted within a steel body shell. The oxygen sensing element is located within a thin-walled cavity at the tip of the ceramic insulator from which a plurality of passages extend to the terminal-pin portion of the ceramic insulator. The electrode lead wires from the oxygen sensing element in the passages may be joined with other electrical lead wires that extend through the passages to terminal pins located in the terminal-pin portion of the insulator. In prior ceramic insulator designs, the lead wires have been bent quite extensively during insertion of the oxygen sensing element electrode lead wires into the passages in the insulator in the process of sensor fabrication. The present invention provides an improved ceramic insulator design for an exhaust gas oxygen sensor of the type described above for use in the oxygen sensing element operating temperature range from about 350° C. to about 850° C.

In accordance with the invention, an exhaust gas sensor body is adapted for connection to the exhaust conduit of an internal combustion engine. A ceramic insulator having a projecting portion for supporting the oxygen sensing element of the sensor is provided. The insulator also has a terminal-pin portion. The ceramic insulator is received within the body and positioned such that the projecting portion is adapted to project into the exhaust conduit when the body is connected thereto as adapted therefor. The projecting portion of the insulator is of circular cross-section and has a plurality of passages extending therefrom to the terminal-pin portion of the insulator. The passages are of substantially equal diameter and have their centers located substantially equidistant from the axis of the projecting portion.

The ceramic insulator projecting portion also has a pedestal of preferably circular cross-section. The pedestal has a radius smaller in length than the distance from the axis of the projecting portion to the centers of the passages in the insulator.

An oxygen sensing element, preferably titania, is positioned adjacent the pedestal. The oxygen sensing element is responsive to the partial pressure of oxygen in exhaust gases and has a plurality of electrode lead wires connected thereto for use in measuring its varying electrical characteristics. The electrode lead wires each extend into the passages in the insulator, the pedestal thereon restricting the bending of the lead wires in the region between the oxygen sensing element and the passages.

The invention may be better understood by reference to the detailed description which follows and to the drawings.

BRIEF DESCRIPTION OF THE DRAWINGS

FIG. 1 is an elevational view of a titania exhaust gas oxygen sensor suitable for installation in the intake manifold of an internal combustion engine;

FIG. 2 is a sectional end view, taken along the line II—II in FIG. 1, and is shown in an enlarged scale;

FIG. 3 is a sectional view, taken along the line III—III in FIG. 2, showing the internal structure of the sensor of FIGS. 1 and 2 also on an enlarged scale; and FIG. 4 is a sectional view taken along the line IV—IV in FIG. 2 and shows the oxygen sensing element of the sensor of FIG. 1 and the ceramic insulator thereof along with the associated electrode lead wires.

DETAILED DESCRIPTION

With particular reference now to FIGS. 1-4, wherein like numerals refer to like parts in the several views, there is shown a complete titania exhaust gas sensor assembly generally designated by the numeral 10. The sensor 10 includes a steel body 12, which may be substantially identical to a commercially available spark plug body having a threaded portion 14 for engagement with a suitable threaded aperture provided within the exhaust system or exhaust conduit of an internal combustion engine (not shown). In most cases, the sensor 10 would be installed in an aperture at a location in the exhaust manifold or conduit near the flange that would connect to an exhaust pipe. A ceramic insulator 16 of circular cross-section extends through the body 12 and has a tapered portion 26 projecting outwardly from the body 12 into the volume defined by the boundaries of a perforated protection tube 18. The projecting portion 26 of the insulator, among other things, acts as a support structure for an oxygen sensing element 46 and a thermistor 48. There are three longitudinal passages, 20, 22, and 24 extending from the projecting end 26 of the ceramic insulator to its opposite terminal-pin portion or end 28. Wires 30, 32 and 34 are located in the respectively corresponding passages 20, 22 and 24 and are of a heat resistance character preferably being made from an alloy such as 80% nickel-20% chromium wire. These electrically conductive wires are welded to precious-metal, primarily platinum, electrode lead wires 40, 42 and 44, which are embedded in the disc-shaped ceramic, metal oxide, oxygen sensing and thermistor elements 46 and 48.

Element 46 is a ceramic titania $O_2$ sensor responsive to the partial pressure of oxygen in the gaseous medium to which this element is exposed. Sensor element 46 may be fabricated in accordance with the teachings of commonly-assigned U.S. Pat. No. 3,886,785 issued June 3, 1975, and 3,932,246 issued Jan. 13, 1976, both in the names of Stadler et al. With regard to the fabrication of the oxygen sensing element 46, it is suggested that consideration be given to the teachings of commonly-assigned and previously or concurrently-filed patents, relating to exhaust gas sensors or thermistors, expected to issue subsequent to the filing date of this patent application.

The element 48 is a thermistor. The thermistor may be made from titania ceramic material of greater density, near its theoretical density, than the density of the porous titania oxygen sensor 46. Alternatively, the thermistor 48 may be constructed in accordance with the teachings of copending and commonly-assigned U.S. patent application Ser. No. 857,498 filed Dec. 5, 1977 in the names of Logothetis, Laud and Park and entitled "Rare Earth-Yttrium, Transition Metal Oxide Thermistors". The thermistor 48 is intended to provide temperature compensation in accordance with the circuitry of the preferred form illustrated and described in commonly-assigned and concurrently-filed U.S. patent application Ser. No. 005,422 filed Jan. 22, 1979 in the names of E. T. Heiney and S. R. Merchant and entitled "Exhaust Gas Sensor Electrical Circuit Improvement". The sensor of FIGS. 1 through 4 is intended to be used in conjunction with electronic circuitry for closed-loop feedback control of the amount of fuel supplied to an internal combustion engine. The sensor indicates whether or not the exhaust gases contain a substantial amount of HC and CO or whether instead there is a substantial amount of $CO_2$, $H_2O$ and $O_2$, thereby indicating whether or not the air/fuel ratio of the mixture supplied to the engine air/fuel rich or lean with respect to the stoichiometric value of about 14.7 parts of air to each part of fuel by weight. This air/fuel ratio typically is expressed as a normalized air/fuel ratio lambda, wherein the actual ratio is divided by the stoichiometric value and the stoichiometric ratio is therefore represented as 1.0 in accordance with well-known practice.

The exhaust gas sensor 10 has terminals 50, 52 and 54 designed for connection to external circuitry as specified above to enable it to be used in a feedback fuel control system. The exhaust gas sensor 10 has the passages 20, 22 and 24 having enlarged portions at the terminal-pin end of the ceramic insulator in which the terminal pins 50, 52 and 54 are received. The electrode lead wires from the ceramic oxygen sensing and thermistor elements 46 and 48 enter the three passages as shown in the drawings to the terminal pins 50, 52 and 54 to which they are electrically connected.

It may be seen that the projecting portion 26 of the insulator 16 has a thin-walled tip portion which forms a cavity in which the oxygen sensing and thermistor elements 46 and 48 are located. This cavity and its walls, in association with the protection tube 18, shield the elements 46 and 48 from direct impingement by exhaust gases flowing through the exhaust conduit of the internal combustion engine associated with the exhaust gas sensor.

The present invention provides a substantial improvement over prior ceramic insulator designs in that a pedestal 60 is provided within the cavity 62 in which the exhaust gas sensing element 46 and the thermistor element 48 are located. The longitudinal axis 64 of the exhaust gas sensor 10 and its ceramic insulator 16 passes through the center of the pedestal 60. The passages 20, 22 and 24 passing in the projecting end 26 and the terminal-pin portion 28 of the ceramic insulator preferably have substantially identical diameters and their centers are located substantially equidistant from the axis 64 of the projecting portion 60 of the ceramic insulator. The pedestal 60 of the ceramic insulator is of circular cross-section and has a radius smaller in length than the distance from the axis 64 of the projecting portion of the insulator to the centers of the passages 20, 22 and 24.

The function of the pedestal 60 is to prevent severe bending of the precious-metal electrode lead wires 40, 42 and 44 which must enter the respectively corresponding passages 20, 22 and 24. Bending of these pure or primarily platinum lead wires causes cold-working of the metal. This induces stresses in the material at its grain boundaries. As is described in commonly-assigned and concurrently-filed U.S. patent application Ser. No. 005,419 filed Jan. 22, 1979 in the name of A. Achari and entitled "Exhaust Gas Sensor Electrode Improvement", the work-hardening or cold-working of the electrode material makes it more susceptible to attack by reactive carbon in the exhaust gases to which it is exposed, and, at elevated temperatures of operation, to oxygen in such exhaust gases. Although the last-mentioned patent application describes means and methods for reducing the susceptibility of the electrode material to such attacks by carbon and oxygen through increases in the amount of energy required to produce the chemical reaction, it remains desirable to minimize the cold-working and work-hardening of the electrode material through the use of the pedestal 60 or equivalent means associated with the ceramic insulator 16.

The pedestal 60 is of cylindrical shape as shown in the preferred form. However, it is anticipated that the invention may be practiced utilizing a pedestal 60 of other than cylindrical shape. For example, a cone or frustoconically-shaped pedestal 60 may be provided extending from or adjacent to the ends 66 of the passages 20, 22 and 24 to a point or surface in a location such as that indicated at 68 in FIG. 4. This conically-shaped pedestal may include means, such as a chamfer at the points 66 or a groove extending therefrom to the plane surface 68, for guiding and supporting the electrode lead wires during and after their insertion in the exhaust gas sensor.

Based upon the foregoing description of the invention, what is claimed is:

1. An improved exhaust gas oxygen sensor of the type adapted for installation in a conduit for conveying exhaust gases from an internal combustion engine, the improved sensor being responsive to the partial pressure of oxygen in the exhaust gases to which the sensor is exposed and having an electrical characteristic which varies, when the sensor is at operating temperatures in the range from about 350° C. to about 850° C., with the partial pressure of oxygen in the exhaust gases, the sensor comprising:

a body adapted for connection to the exhaust conduit of an internal combustion engine;

a ceramic insulator having a projecting portion and a terminal-pin portion, the ceramic insulator being received within the body and being positioned such that the projecting portion is adapted to project into the exhaust conduit when the body is connected thereto as adapted therefor, the projecting portion of the insulator being of circular cross-section and having a plurality of passages extending therefrom to the terminal-pin portion of the insulator, the passages having their centers located substantially equidistant from the axis of the projecting portion, the insulator projecting portion having a pedestal of circular cross-section, and the pedestal having a radius smaller in length than the distance from the axis of the projecting portion to the centers of the passages;

an oxygen sensing element supported by the projecting portion of the insulator and positioned adjacent the pedestal thereof, the oxygen sensing element being responsive to the partial pressure of oxygen in exhaust gases, the oxygen sensing element having a plurality of electrical lead wires connected thereto, the electrical lead wires each extending through a different one of the passages in the insulator to the terminal-pin portion thereof, the pedestal of the insulator restricting bending of the electrical lead wires in the region between the oxygen sensing element and the passages.

2. An improved exhaust gas oxygen sensor in accordance with claim 1, wherein the pedestal of the ceramic insulator is cylindrical in shape.

3. An improved exhaust gas oxygen sensor according to claim 1, wherein the pedestal of the ceramic insulator is conical or frusto-conical in shape.

4. An improved exhaust gas oxygen sensor in accordance with claim 1, wherein the pedestal of the ceramic insulator is defined by a plane intersecting the axis of the projecting portion of the ceramic insulator and a surface extending from the plane to points at which the passages in the projecting portion of the insulator end.

* * * * *